(12) United States Patent
Nassiri et al.

(10) Patent No.: US 7,972,339 B2
(45) Date of Patent: Jul. 5, 2011

(54) SYRINGE FOR BIOMATERIAL

(75) Inventors: Nasser Nassiri, Levallois-Perret (FR); Yves Cirotteau, Paris (FR); Alberto Jussmann, Antony (FR)

(73) Assignee: Bio Holdings International Limited, Tortola (VG)

( * ) Notice: Subject to any disclaimer, the term of this patent is extended or adjusted under 35 U.S.C. 154(b) by 0 days.

(21) Appl. No.: 11/914,028

(22) PCT Filed: May 9, 2006

(86) PCT No.: PCT/FR2006/050422
§ 371 (c)(1),
(2), (4) Date: Jul. 11, 2008

(87) PCT Pub. No.: WO2007/003799
PCT Pub. Date: Jan. 11, 2007

(65) Prior Publication Data
US 2009/0137946 A1    May 28, 2009

(30) Foreign Application Priority Data

May 10, 2005    (FR) ..................... 05 04659

(51) Int. Cl.
*A61B 17/00* (2006.01)
(52) U.S. Cl. .......................... 606/92; 606/94
(58) Field of Classification Search ............ 604/57–64; 606/92–94, 95; 623/23.58, 23.59, 23.61, 623/23.62
See application file for complete search history.

(56) References Cited

U.S. PATENT DOCUMENTS

| | | | | |
|---|---|---|---|---|
| 4,653,487 A * | 3/1987 | Maale | | 606/62 |
| 4,671,263 A * | 6/1987 | Draenert | | 606/94 |
| 4,871,094 A * | 10/1989 | Gall et al. | | 222/386 |
| 5,292,515 A * | 3/1994 | Moro et al. | | 424/422 |
| 5,752,940 A | 5/1998 | Grimard | | |
| 5,871,484 A * | 2/1999 | Spievack et al. | | 606/60 |
| 6,436,143 B1 | 8/2002 | Ross et al. | | |
| 6,679,890 B2 * | 1/2004 | Margulies et al. | | 606/94 |
| 7,250,055 B1 * | 7/2007 | Vanderwalle | | 606/92 |
| 7,608,062 B2 * | 10/2009 | Sweeney | | 604/264 |
| 2001/0021852 A1 | 9/2001 | Chappius | | |
| 2004/0068267 A1 * | 4/2004 | Harvie et al. | | 606/92 |
| 2004/0243137 A1 * | 12/2004 | Gorek | | 606/92 |

FOREIGN PATENT DOCUMENTS

| | | |
|---|---|---|
| FR | 2 820 631 | 2/2001 |
| WO | WO 01/56515 A2 | 8/2001 |
| WO | WO 03/037165 A2 | 5/2003 |

* cited by examiner

*Primary Examiner* — Nicholas D Lucchesi
*Assistant Examiner* — Gerald Landry, II
(74) *Attorney, Agent, or Firm* — Leffert Jay & Polglaze, P.A.

(57) ABSTRACT

An injector device for percutaneously injecting biomaterial in the form of particles of different sizes or in the form of paste includes a trocar (12) of generally cylindrical shape presenting a open first end with a sharp edge, the wall of the first end presenting at least one orifice (36, 38) for passing the biomaterial, and a second end (42) that is likewise open; a reservoir (14) for receiving the biomaterial, the reservoir including a part (20) of substantially cylindrical shape having two open ends, the cylindrical part being capable of being inserted at least in a portion of the trocar via the second end thereof; removable plugs for closing both ends of the reservoir; and a piston (16) insertable in the cylindrical part when the plugs are removed, the piston being capable of sliding in the cylindrical part and in the first end of the trocar.

21 Claims, 2 Drawing Sheets

SYRINGE FOR BIOMATERIAL

The present invention relates to a percutaneous injector device of the syringe type for percutaneous injection of a biomaterial in the form of particles (of different sizes) or in the form of a paste.

More precisely, the invention relates to a device serving to inject, in particular into the inside of a bone, a biomaterial, e.g. such as natural coral or other analogous materials, e.g. calcium salts used alone or mixed with other substances: bone morphogenic protein (BMP), bone marrow extracts, cultured or autologous osteogenic cells, cements, etc. . . . in the form of small particles or of a paste.

The composition may be injected in the form of a powder of particles or in the form of a paste.

With certain bone pathologies, whether congenital or acquired, the outer portion of the bone conserves its integrity and its mechanical properties. In others, and in particular in diseases associated with dimineralization or defective mineralization of the bone, it can thus happen that phenomena of degeneration occur in the internal portion, possibly leading to the formation of cavities inside the bone of various greater or smaller sizes. Even if this situation does not lead immediately to an incapacitating effect for the subject, the presence of cavities within the bone reduces the strength of the bone, e.g. at the top end of the femur, to an extent that increases with increasing extent of said cavities. This situation can lead to risks of fractures that are particularly severe when loss of bone is large.

Concerning local treatment for preventative purposes of bone diseases associated with demineralization of, or with lack of mineralization of, the bone, and in particular treatment and prevention of fracture of the neck of the femur as directly associated with such diseases, proposals have already been made in European patent EP 0 649 309 to use particles of biomaterial to fill in the cavities formed inside bones so as to regenerate the inside portion of the bone for the purposes of restarting the process bone remineralization, and thus of restoring to the bone its initial strength or to strength that is close to said initial strength.

The object of such preventative action is to perform local treatment of diseases associated with demineralization or with lack of mineralization of the bone by locally providing medication (in particular the biomaterials as specified in the patent filed earlier by the Applicants) long before the disease leads to fractures occurring. Such fractures arise more usually in old people and are very complicated, immobilizing patients for several months with severe consequences on the function of the hips and on the life of patients.

The technique presently used for performing the operation consists in piercing an orifice through the outer portion of the bone leading to the internal cavity or cavities, and then using a spatula or a curette, to introduce the particles of biomaterial as well as possible into the orifice so that the particles fill the internal cavity inside the bone induced by demineralization of the bone. That operation is relatively lengthy and difficult and it is not possible to be sure that the cavity has indeed been completely filled with particles of biomaterial.

There thus exists a real need to have a device that enables the orifice to be made through the outer portion of the bone and simultaneously enables particles of biomaterial to be injected into the internal cavity inside the bone.

An object of the present invention is to provide an injector device for percutaneously injecting biomaterial having the form and the characteristics as described above in the present specification, and satisfying the needs mentioned above.

Such injection is performed either during an operation on a fracture, but on the other side that has not fractured, or else in a single operation and on purely preventative grounds, on both sides that have not fractured, after determining by osteodensitometry that bone loss has occurred, and for example after locating where bone loss extends with the help of a three-dimensional X-ray method. Such surgery is carried out with the patient's agreement in accordance with the techniques of good practice.

According to the invention, this object is achieved by a device for injecting biomaterial in the form of particles or of a paste, and that is characterized in that it comprises:

a trocar of generally cylindrical shape presenting an open first end with a sharp edge, the wall of said first end presenting at least one orifice for passing the biomaterial, and a second end that is likewise open;

a reservoir for receiving said biomaterial, the reservoir comprising a part of substantially cylindrical shape having two open ends, said cylindrical part being capable of being inserted at least in a portion of the trocar via the second end thereof, and removable means for closing both ends of the reservoir; and a piston insertable in said cylindrical part when said closure means are removed, said piston being capable of sliding in said cylindrical part and in the first end of the trocar.

It will be understood that because of the presence of the sharp edge at the end of the trocar, the injector device itself serves to make the orifice in the outer portion of the bone. Furthermore, the reservoir that can be engaged in the trocar enables the biomaterial-based composition to be prepared prior to being injected into the bone. As explained below, as a general rule, the particles of biomaterial need to be mixed with some other ingredient. Finally, the piston enables sufficient pressure to be applied to the biomaterial contained in the reservoir for the particles leaving the trocar via its open end and through the orifices it includes to ensure, under the effect of said pressure, appropriate filling of the internal cavity induced within the bone by its demineralization.

Preferably, the second end of the trocar includes external means such as notches or holes to enable the trocar to be turned about its longitudinal axis so as to encourage making the orifice through the outer portion of the bone.

Also preferably, the device further includes a percussion endpiece that can be fastened, in temporary manner prior to putting the reservoir into place, on the second end of the trocar so as to enhance the effect of cutting the outer portion of the bone with the help of the sharp end of the trocar.

Also preferably, the inside wall of the trocar includes, close to its second end, a shoulder for limiting the extent to which the reservoir can be engaged within the trocar. Similarly, the outside wall of the trocar includes, close to its first end, a shoulder for limiting the extent to which the end of the trocar can be engaged in the bone.

Also preferably, the inside diameter of the reservoir and the inside diameter of the first end of the trocar that extends between the internal shoulder and the cutting edge are substantially equal so as to avoid any discontinuity in the flow of particles of biomaterial under drive from the piston.

Other characteristics and advantages of the invention appear better on reading the following description of an embodiment given by way of non-limiting examples. The description refers to the accompanying drawings, in which.

Figure 1A:
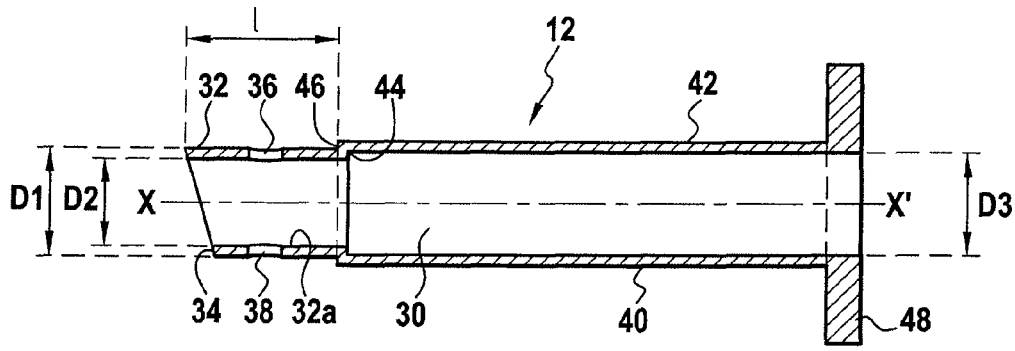
FIG. 1A is a longitudinal section view of a trocar.

With reference initially to FIGS. 1 to 4, there follows a description of the various component elements of the biomaterial injector device.

As mentioned above, the injector device is constituted essentially by a trocar 12, a biomaterial reservoir 14, and a piston 16. The injector device preferably also includes a removable percussion endpiece 18 and plugs for closing the cylindrical part 20 of the reservoir, these plugs being referenced 22 and 24.

The trocar 12 of the injector device 10 shown in FIG. 1A is generally cylindrical in shape with an internal recess 30. The trocar 12 has a first end 32 of outside diameter D2 and of inside diameter D1. The edge 34 of the first end 32 is sharp, and this edge is preferably disposed in a plane that is not orthogonal to the axis X,X' of the trocar. This first end 32 also has orifices 36 and 38 in its wall of size sufficient to allow particles of biomaterial to pass therethrough. The trocar 12 has a middle portion 40 and a second end 42. The inside diameter of the middle portion 40 and of the second end 42 is referenced D3 and is greater than the inside diameter D1 of the first end 32. The inside wall of the trocar thus defines an internal shoulder 44. This difference in inside diameter also defines an external shoulder 46. In the example described, the inside diameter D1 of the first end of the trocar is equal to 12 millimeters (mm). More generally, this diameter lies in the range 9 mm to 15 mm. The length l of the end of the trocar is 20 mm in the example described.

Figure 1B:
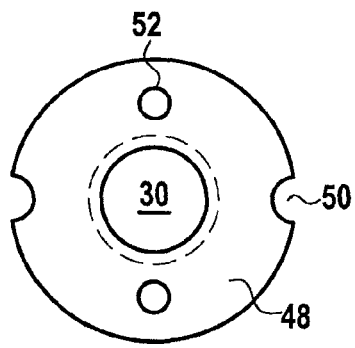
FIG. 1B is a view of the second end of the trocar in a preferred embodiment.

The second end 42 of the trocar includes an outwardly-directed collar 48 serving to enable the trocar to be manipulated, possibly with the help of an instrument or a tool. In FIG. 1B, there is shown a collar 48 that advantageously includes external notches such as 50 or orifices 52 serving to engage tools for setting the trocar into rotation so as to improve the effect of its sharp edge 34.

The reservoir 14 is constituted by the body 20 which is cylindrical in shape with an inside diameter D4 and an outside diameter D5. The first end 54 of the cylindrical body 20 is open, as is its first end 56. The first end 56 is provided with an outwardly-directed collar 58. In order to enable the reservoir to be closed, the device also includes end plugs 22 and 24. The end plug 22 for co-operating with the first end 54 of the cylindrical body 20 presents an end wall 22a and a peripheral skirt 22b defining an internal cavity of diameter D'5 enabling the plug 22 to be fastened on the end 54 by elastic deformation. Similarly, the second end plug 24 comprises an end wall 24a and a peripheral skirt 24b defining an internal cavity of diameter D'6 such that the plug 24 can be fastened on the collar 58 by elastic deformation.

Figure 4:
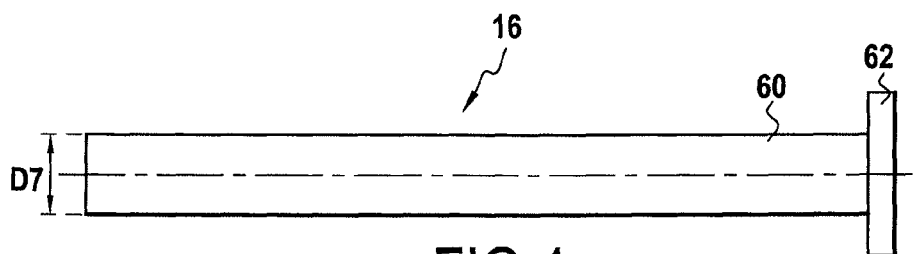
FIG. 4 is a side view of the piston.

FIG. 4 shows the piston or pusher 16 which is solid. It presents a constant outside diameter D7, and at its end 60 it is fitted with a collar 62 to facilitate the action of the operator on the pusher 16.

Figure 2:
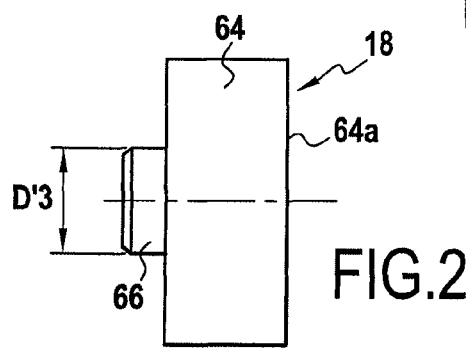
FIG. 2 is a side view of the percussion endpiece.
Figure 3A:
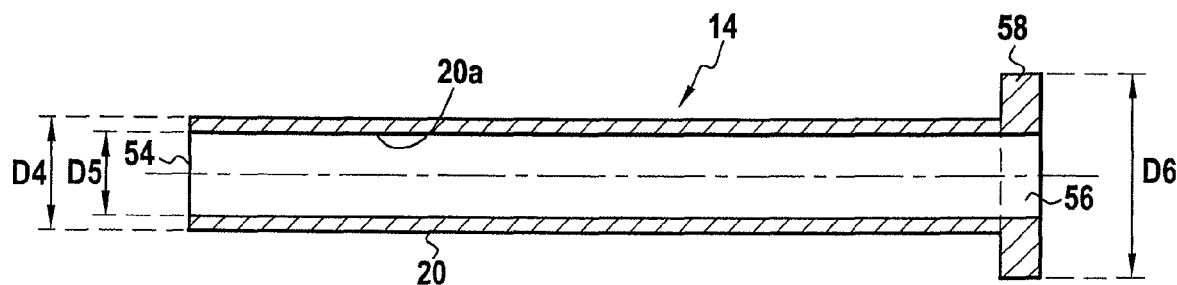
FIG. 3A is a longitudinal section view of the cylindrical part of the reservoir.
Figure 3B:
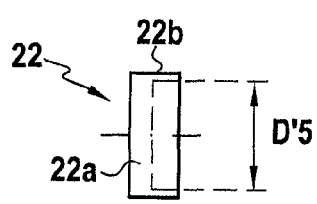
FIGS. 3B and 3C are side views of the closure means that can be placed at the ends of the cylindrical part of the reservoir.
Figure 3C:
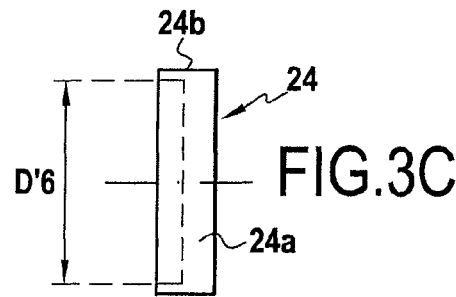

The injector device 10 preferably also includes a percussion endpiece 18. This endpiece is shown in FIG. 2 and comprises a cylindrical main body 64 defining a percussion face 64a, and a fastener extension 66 that projects from the body 64 and presents an outside diameter D'3 slightly greater than the inside diameter D3 of the second end of the trocar so as to enable the percussion endpiece 18 to be fastened releasably on the second end of the trocar.

It should be added that the diameter D1 of the inside wall 32a of the end 32 of the trocar and the diameter D4 of the inside wall 20a of the cylindrical body 20 of the reservoir are substantially equal. Thus, when the reservoir 14 is introduced into the trocar 12, the resulting internal passage presents a wall that is substantially smooth, i.e. not having any obstacles. Naturally, it should be added that the outside diameter D7 of the piston 16 is slightly smaller than the inside diameter D4 of the cylindrical body 20 of the reservoir such that the piston 16 can slide freely inside the cylindrical body 20 and inside the end 32 of the trocar. Nevertheless, the difference between the two diameters is small so as to avoid allowing particles of biomaterial to become jammed between the outside face of the piston 16 and the inside face of the reservoir 14.

Figure 1C:
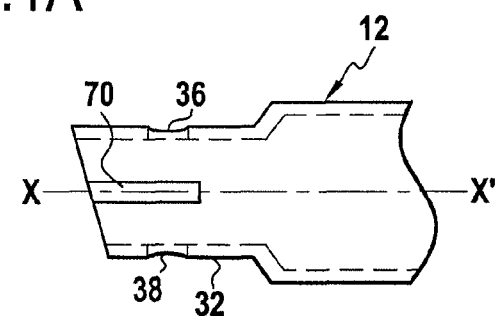
FIG. 1C is a side view of a preferred embodiment of the first end of the trocar.

FIG. 1C shows a preferred embodiment for the end 32 of the trocar 12. In this embodiment, the outside face of the end 32 may be fitted with blades 70 extending parallel to the axis X,X' of the trocar. The or each blade 70 is naturally disposed between the orifices 36 and 38. The blade(s) serve(s) to "scrape" the wall of the orifice made with the help of the trocar by turning the trocar.

Figure 5:
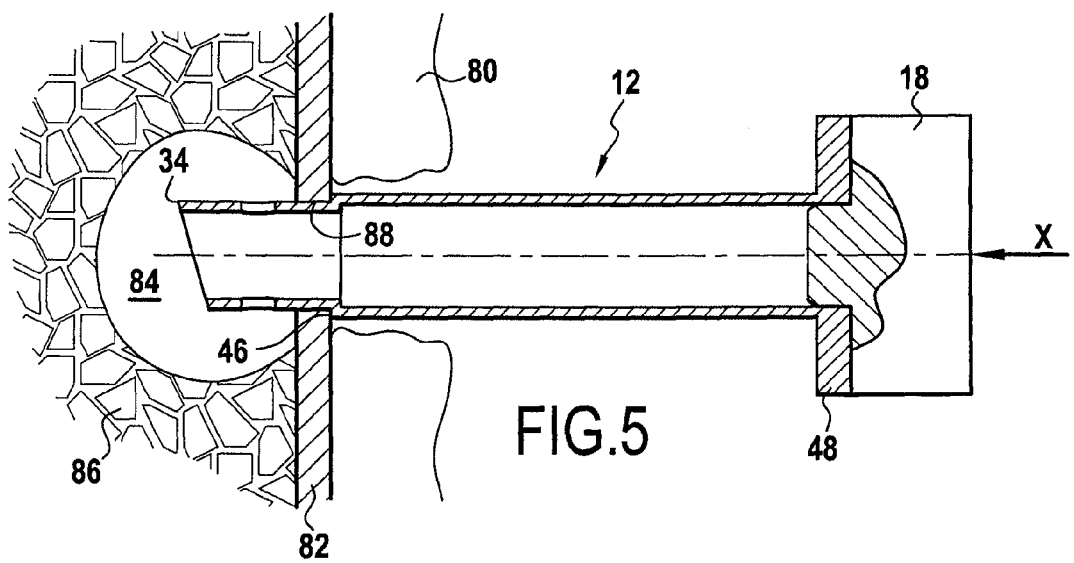
FIG. 5 shows the first stage in utilization of the injector device showing more particularly perforation in the outside wall of the bone and the use of the percussion endpiece.
Figure 6:
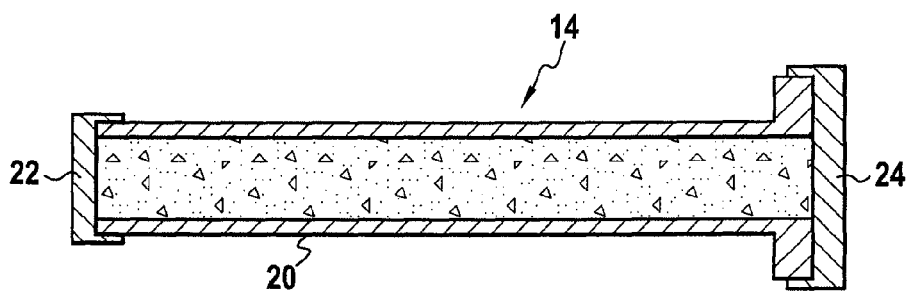
FIG. 6 shows the reservoir closed at its ends in order to make a preparation based on biomaterial.
Figure 7:
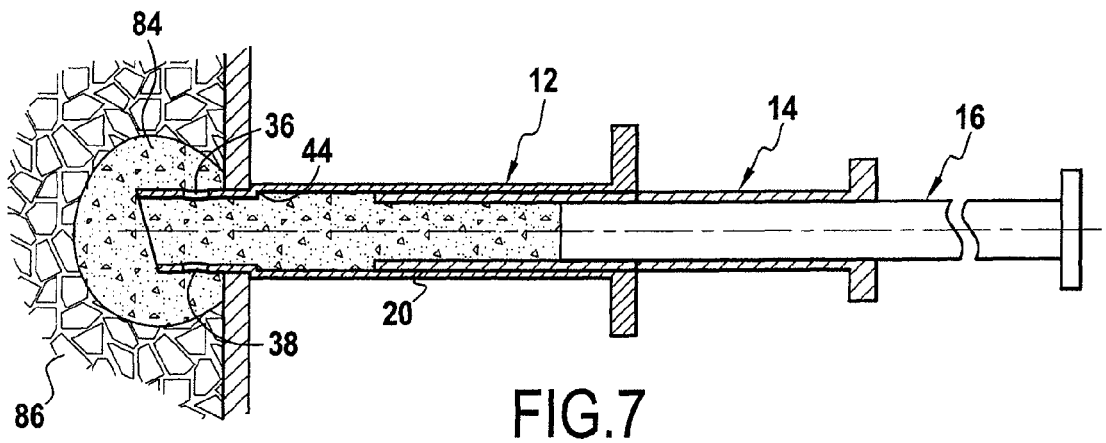
FIG. 7 shows the injector device as a whole ready for proceeding with introducing biomaterial into the internal cavity of the bone as induced by demineralization of the bone.

With reference below to FIGS. 5 to 7, there follows a description of the use of the injector device for percutaneous injection of biomaterial.

Initially, the surgeon uses a image intensifier to identify the entry point for the trocar 12. A scalpel is used to make a small cutaneous incision to enable the instrument to be introduced. Using the image intensifier, the surgeon passes the trocar through the outer portion of the bone in which biomaterial is to be injected. That is to say behind which a cavity 84 has formed in the inside portion 86 of the bone. To make an orifice 88 in the outside wall of the bone 82, the surgeon naturally makes use of the sharp end 34 of the trocar 12. To do this, it is possible to be assisted by a tool that co-operates with the notches 50 or the orifices 52 provided in the collar 48 of the trocar so as to impart rotary movement to the trocar about its longitudinal axis X,X'. The surgeon can also put the percussion endpiece 18 into place so as to enable greater pressure to be exerted on the bone via the sharp edge 34 of the trocar by applying blows from a suitable instrument.

Once the orifice 88 has been fully prepared, the trocar 12 bears against the outside of the bone via the external shoulder 46 and the end 32 of the trocar penetrates into the inside of the cavity 84 that is to be treated. The surgeon then prepares, in the reservoir, the biomaterial-based composition that is to be used. This composition usually consists in a certain quantity of particles of biomaterial, such as natural coral, to which the surgeon adds, for example, a certain quantity of bone marrow to encourage regeneration of the internal portion of the bone with the help of the biomaterial. To do this, the surgeon puts the plugs 22 and 24 successively into place at the ends of the cylindrical body 20, thus enabling the assembly to be shaken sufficiently to obtain a completely uniform mixture.

Once the operation has been completed, the surgeon naturally removes the plugs 22 and 24 from the reservoir 14 and places the cylindrical body 20 inside the trocar 12 until the end 54 of the cylindrical body 20 comes into abutment against the internal shoulder 44 of the trocar. The reservoir 14 containing the biomaterial-based composition is thus firmly held in the trocar 12. It then suffices to insert the piston 16 into the end of the cylindrical body 20 so as to cause the particles of biomaterial to be expelled through the open end of the trocar and through its lateral orifices 36 and 38. The pressure exerted on the biomaterial-based composition by the piston 16 serves to ensure that the biomaterial fills appropriately the cavity 84 in the internal portion of the bone. Furthermore, the fact that the first end of the trocar is open and that said first end also includes lateral orifices 36 and 38 makes it easier to extract the biomaterial from the trocar and enter it into the cavity 84.

In the above description, it is assumed more particularly that the biomaterial is in the form of particles. The device should also be used with a biomaterial in the form of a paste, so long as its viscosity is suitable.

The invention claimed is:

1. An injector device for percutaneously injecting biomaterial in the form of particles of different sizes or of a paste, said device comprising:
    a trocar of generally cylindrical shape presenting an open first end with a sharp edge for drilling bone walls, a wall of said first end having lateral orifices for passing the biomaterial, and a second end that is likewise open;
    a reservoir for receiving said biomaterial, said reservoir comprising a part of substantially cylindrical shape having two open ends, said cylindrical part being capable of being inserted at least in a portion of the trocar via the second end thereof and having an inside diameter that is substantially constant over its entire length;
    removable means for totally closing both ends of the reservoir; and
    a piston insertable in said cylindrical part when said closure means are removed, said piston being capable of sliding in said cylindrical part over the entire length thereof and in the first end of the trocar;
    wherein an outside face of the first end of the trocar includes at least one blade extending parallel to the axis of the trocar.

2. A device according to claim 1, wherein said second end of the trocar includes external means for enabling the trocar to be turned about its longitudinal axis.

3. A device according to claim 2, wherein said means for enabling turning the trocar comprise an outwardly-directed collar disposed at the second end of the trocar, said collar including means for co-operating with a turning tool.

4. A device according to claim 1, further including a percussion endpiece suitable for being releasably fastened on the second end of the trocar when said reservoir is not inserted therein.

5. A device according to claim 1, wherein an inside wall of the trocar includes, close to its first end, an abutment for limiting the extent to which the cylindrical part of the reservoir can be engaged.

6. An injector device for percutaneously injecting biomaterial in the form of particles of different sizes or of a paste, said device comprising:
    a trocar of generally cylindrical shape presenting an open first end with a sharp edge for drilling bone walls, a wall of said first end having lateral orifices for passing the biomaterial, and a second end that is likewise open;
    a reservoir for receiving said biomaterial, said reservoir comprising a part of substantially cylindrical shape having two open ends, said cylindrical part being capable of being inserted at least in a portion of the trocar via the second end thereof and having an inside diameter that is substantially constant over its entire length;
    removable means for totally closing both ends of the reservoir; and
    a piston insertable in said cylindrical part when said closure means are removed, said piston being capable of sliding in said cylindrical part over the entire length thereof and in the first end of the trocar;
    wherein an inside wall of the trocar includes, close to its first end, an abutment for limiting the extent to which the cylindrical part of the reservoir can be engaged; and
    wherein said abutment is a shoulder in the inside wall of the trocar.

7. A device according to claim 6, wherein the inside diameter of the cylindrical part of the reservoir is substantially equal to the inside diameter of the portion of said trocar that extends between said internal shoulder and said sharp edge.

8. A device according to claim 7, wherein the outside wall of the trocar includes a shoulder corresponding to said internal shoulder, to limit the extent to which the trocar can be engaged.

9. A device according to claim 1, wherein the sharp edge of the first end of the trocar lies in a plane that is not orthogonal to the longitudinal axis of the trocar.

10. A device according to claim 1, wherein the inside diameter of the first end of the trocar lies in the range 9 mm to 15 mm.

11. A device according to claim 1, wherein an interior of the reservoir is totally closed by the closure means and a cylindrical wall of the reservoir.

12. A device according to claim 5, wherein said abutment is a shoulder in the inside wall of the trocar.

13. A device according to claim 12, wherein the inside diameter of the cylindrical part of the reservoir is substantially equal to the inside diameter of the portion of said trocar that extends between said internal shoulder and said sharp edge.

14. A device according to claim 13, wherein the outside wall of the trocar includes a shoulder corresponding to said internal shoulder, to limit the extent to which the trocar can be engaged.

15. A device according to claim 6, wherein said second end of the trocar includes external means for enabling the trocar to be turned about its longitudinal axis.

16. A device according to claim 15, wherein said means for enabling turning the trocar comprise an outwardly-directed collar disposed at the second end of the trocar, said collar including means for co-operating with a turning tool.

17. A device according to claim 6, further including a percussion endpiece suitable for being releasably fastened on the second end of the trocar when said reservoir is not inserted therein.

18. A device according to claim 6, wherein an outside face of the first end of the trocar includes at least one blade extending parallel to the axis of the trocar.

19. A device according to claim 6, wherein the sharp edge of the first end of the trocar lies in a plane that is not orthogonal to the longitudinal axis of the trocar.

20. A device according to claim 6, wherein the inside diameter of the first end of the trocar lies in the range 9 mm to 15 mm.

21. A device according to claim 6, wherein an interior of the reservoir is totally closed by the closure means and a cylindrical wall of the reservoir.

* * * * *